(12) United States Patent
Young

(10) Patent No.: US 11,723,812 B2
(45) Date of Patent: Aug. 15, 2023

(54) ORGANIC COTTON SURFACE NURSING PAD

(71) Applicant: POSH 365 US, INC., Eastvale, CA (US)

(72) Inventor: Christina H. Young, Eastvale, CA (US)

(73) Assignee: POSH 365 US, INC., Irvine, CA (US)

(*) Notice: Subject to any disclaimer, the term of this patent is extended or adjusted under 35 U.S.C. 154(b) by 908 days.

(21) Appl. No.: 16/720,421

(22) Filed: Dec. 19, 2019

(65) Prior Publication Data

US 2020/0197237 A1 Jun. 25, 2020

Related U.S. Application Data

(60) Provisional application No. 62/782,017, filed on Dec. 19, 2018.

(51) Int. Cl.
| | | |
|---|---|---|
| *A61F 13/14* | (2006.01) | |
| *A61F 13/53* | (2006.01) | |
| *A61F 13/15* | (2006.01) | |
| *A61F 13/511* | (2006.01) | |

(52) U.S. Cl.
CPC .......... *A61F 13/141* (2013.01); *A61F 13/53* (2013.01); *A61F 2013/1517* (2013.01); *A61F 2013/51139* (2013.01); *A61F 2013/530007* (2013.01); *A61F 2013/5307* (2013.01); *A61F 2013/530029* (2013.01); *A61F 2013/530481* (2013.01)

(58) Field of Classification Search
CPC .......... A61F 13/141; A61F 2013/15016; A61F 2013/1517; A61F 2013/51139; A61F 2013/530007; A61F 2013/530481; A61F 2013/5307; A61F 13/53; A61F 2013/530029
See application file for complete search history.

(56) References Cited

U.S. PATENT DOCUMENTS

| | | | | |
|---|---|---|---|---|
| 3,779,190 A | * | 12/1973 | Hower | D05C 17/00 112/475.18 |
| 4,074,721 A | * | 2/1978 | Smits | A61F 13/141 604/377 |
| 7,886,776 B2 | * | 2/2011 | Jung | A61F 13/00038 139/421 |
| 2003/0220048 A1 | * | 11/2003 | Toro | A61F 13/141 450/57 |
| 2006/0288463 A1 | * | 12/2006 | Bernard | A41D 27/12 2/46 |
| 2013/0096525 A1 | * | 4/2013 | Hermansson | A61F 13/4752 604/374 |

* cited by examiner

*Primary Examiner* — Susan S Su
(74) *Attorney, Agent, or Firm* — Risso IP

(57) ABSTRACT

Described is a cotton surface nursing pad having both a proximal side and distal side. The proximal side is formed of a surface layer made of certified organic cotton, while the distal side is formed of a leakproof film later. Sandwiched between the surface layer and leakproof film layer are a first tissue layer, an absorbent core layer, and a second tissue layer. Notably, the absorbent core layer is formed of a combination of super absorbent polymer and fluff pulp, while the certified organic cotton is woven together using a half-cross pattern to form the surface layer.

17 Claims, 4 Drawing Sheets

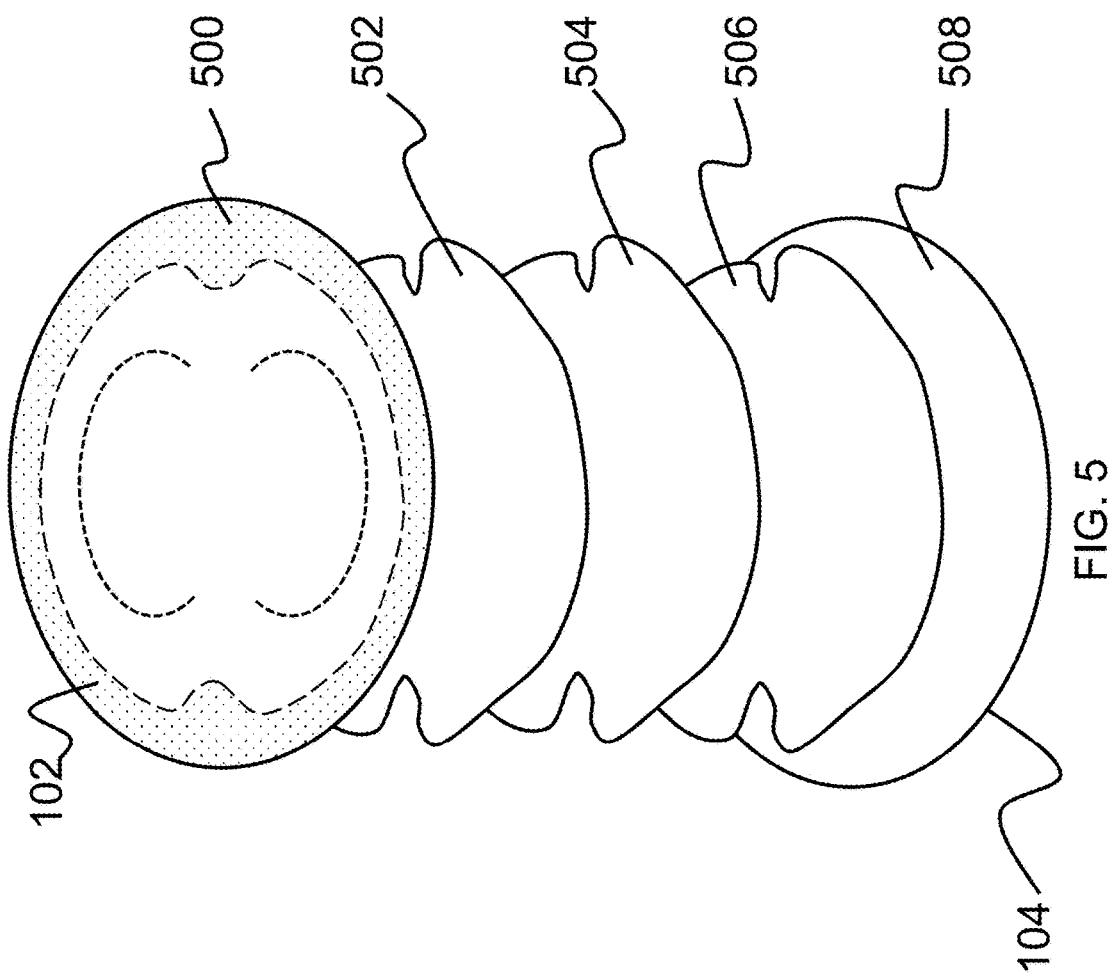

ORGANIC COTTON SURFACE NURSING PAD

CROSS-REFERENCE TO RELATED APPLICATIONS

This is a non-provisional application of U.S. Provisional Application No. 62/782,017, filed on Dec. 19, 2018, the entirety of which is incorporated herein by reference.

BACKGROUND OF THE INVENTION

(1) Field of Invention

The present invention relates to a nursing pad and, more particularly, to an organic cotton surface nursing pad for absorbing excess breast milk.

(2) Description of Related Art

Nursing pads, also referred to as breast pads, are an accessory often used by women to avoid issues from leaking breast milk. Leaking breastmilk can result in circles of wetness on clothing that is embarrassing and can cause irritation. The moisture against the skin can result in irritation or even infection. To avoid this, the nursing pads are placed inside of a user's bra to catch and absorb leaking breast milk, thereby protecting the clothing from leaking breast milk.

While generally operable, existing nursing pads use either synthetic layers/chemicals, or cotton pads that lack sufficient absorbency. Thus, a continuing need exists for a new and improved nursing pad that provides increased absorbency while using organic natural materials for the surface that contacts the skin and nipple where baby feeds from.

SUMMARY OF INVENTION

The present invention relates to a nursing pad and, more particularly, to an organic cotton surface nursing pad with special formulated absorbent core for absorbing excess breast milk. In aspect, the nursing pad includes a proximal side formed of a surface layer, the surface layer being formed of organic cotton. A distal side is also included. The distal side is formed of a leakproof film layer. Importantly, an absorbent core layer is affixed between the surface layer and leakproof film layer.

In yet another aspect, a first tissue layer is adhered between the surface layer and absorbent core layer.

In another aspect, a second tissue layer is adhered between the absorbent core layer and leakproof film layer.

Further, the organic cotton is woven together using a half-cross pattern to form the surface layer.

In another aspect, the absorbent core layer is formed of a combination of super absorbent polymer and fluff pulp.

Additionally, the cotton surface nursing pad has a mass, with the organic cotton forming the surface layer being between 10% and 20% of the mass of the cotton surface nursing pad.

In another aspect, the super absorbent polymer in the absorbent core layer is between 15% to 25% of the mass of the cotton surface nursing pad.

Further, the fluff pulp in the absorbent core layer is between 35% to 50% of the mass of the cotton surface nursing pad.

In yet another aspect, the organic cotton forming the surface layer is approximately 15.5% of the mass of the cotton surface nursing pad.

In another aspect, the super absorbent polymer in the absorbent core layer is approximately 20% of the mass of the cotton surface nursing pad.

In yet another aspect, the fluff pulp in the absorbent core layer is approximately 44% of the mass of the cotton surface nursing pad.

Finally, as can be appreciated by one in the art, the present invention also comprises a method for forming and using the invention described herein.

BRIEF DESCRIPTION OF THE DRAWINGS

The objects, features and advantages of the present invention will be apparent from the following detailed descriptions of the various aspects of the invention in conjunction with reference to the following drawings, where:

FIG. 5 is an exploded-view illustration of the nursing pad according to various embodiments of the present invention, depicting various layers of the nursing pad.

DETAILED DESCRIPTION

Figure 2:
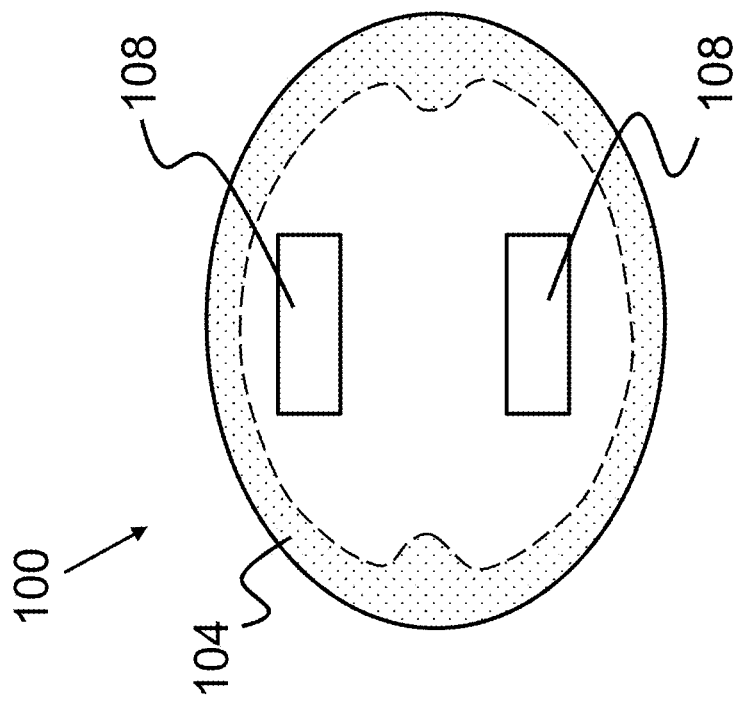
FIG. 2 is an illustration of a distal side of the nursing pad according to various embodiments of the present invention.

The present invention relates to a breast pad and, more particularly, to an organic cotton surface breast pad. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of or" act of in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

The present disclosure provides an organic cotton surface nursing pad for absorbing excess breast milk. While there are cotton nursing pads in the market, existing nursing pads lack the desired absorbency, resulting in dampness/wetness of the cotton nursing pads. As described in further detail below, present invention addresses this issue by having several layers, including an extra absorbent core layer (super absorbent polymer (SAP)) in the back that helps suck the moisture away from the organic cotton surface layer to prevent the very dampness that customers complain about. Testing also shows that approximately 35 milliliters of dripping or at a rate of a natural flow of leaking breast milk passes through the organic cotton surface layer to the absorbent core layer and does not come back out to the organic cotton surface layer under normal wear.

Further, existing nursing pads include a variety of synthetic/chemical layers that rest against the nipple upon which a baby feeds. To provide a more natural surface, the nursing pad according to various embodiments of the present invention desirably includes an organic cotton (certified or otherwise) surface layer. The organic cotton surface layer provides a natural barrier, instead of synthetic layers/chemicals, between the absorbent core layer and the nipple.

Figure 1:
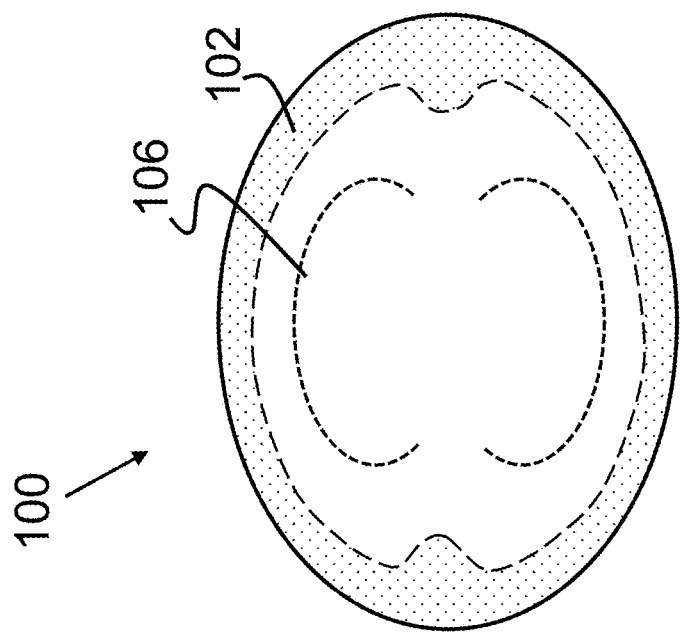
FIG. 1 is an illustration of a proximal side of a nursing pad according to various embodiments of the present invention.

For further understanding, provided with this disclosure are FIGS. 1 through 5. Specifically, and as shown in FIGS. 1 and 2, the nursing pad 100 has a proximal side 102 and a distal side 104. The proximal side 102 is the skin contact side, meaning the side that rests against the user's nipple to absorb excess milk and draw such excess milk into the nursing pad 100. As shown on the proximal side 102, a series of groove marks 106 are formed on the surface. The groove marks 106 are formed on the surface using any suitable mechanism or technique. As a non-limiting example, the groove marks 106 are pressed into the surface layer (described in further detail below) which forms the proximal side 102. The groove marks 106 creates a series of grooves that slows down the overflow of excess milk, allowing the surface layer to more easily capture and absorb excess milk.

Alternatively, the distal side 104 is the outward side, or the side facing away from the user that typically comes into contact with the user's clothing. To assist the nursing pad 100 in sticking to the user's clothing at a desired location, one or more adhesive layers 108 can be affixed with the surface of the distal side 104. The adhesive layers 108 are any suitable material that allows for adhesion of the nursing pad 100 to the user's clothing, a non-limiting example of which includes a hot melt with a release paper.

Figure 4:
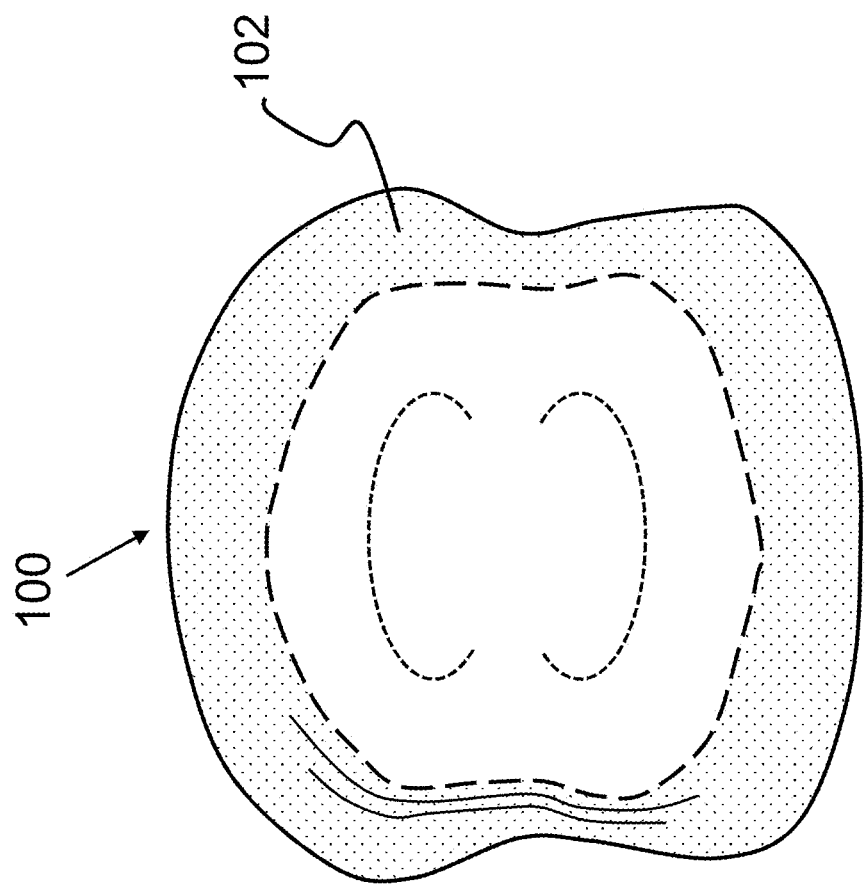
FIG. 4 is a proximal-side illustration of the nursing pad according to various embodiments of the present invention, depicting a contour of the nursing pad.
Figure 3:
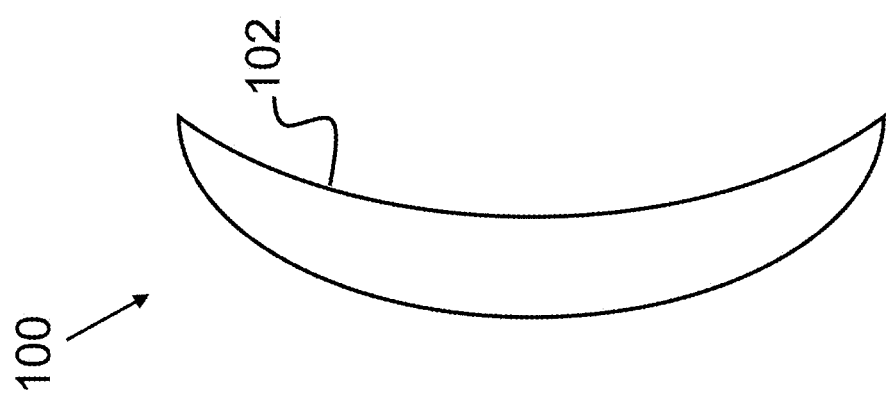
FIG. 3 is a side-view illustration of the nursing pad according to various embodiments of the present invention, depicting a contour of the nursing pad.

In one aspect and as shown in side-view illustration of FIG. 3, the nursing pad 100 is contoured such that the proximal side 102 has a generally concave shape. The concave shape assists the nursing pad 100 in comfortably resting against the user's breast. The contour or curvature is also illustrated in FIG. 4, which depicts the proximal side 102 of the nursing pad 100.

Figure 6:
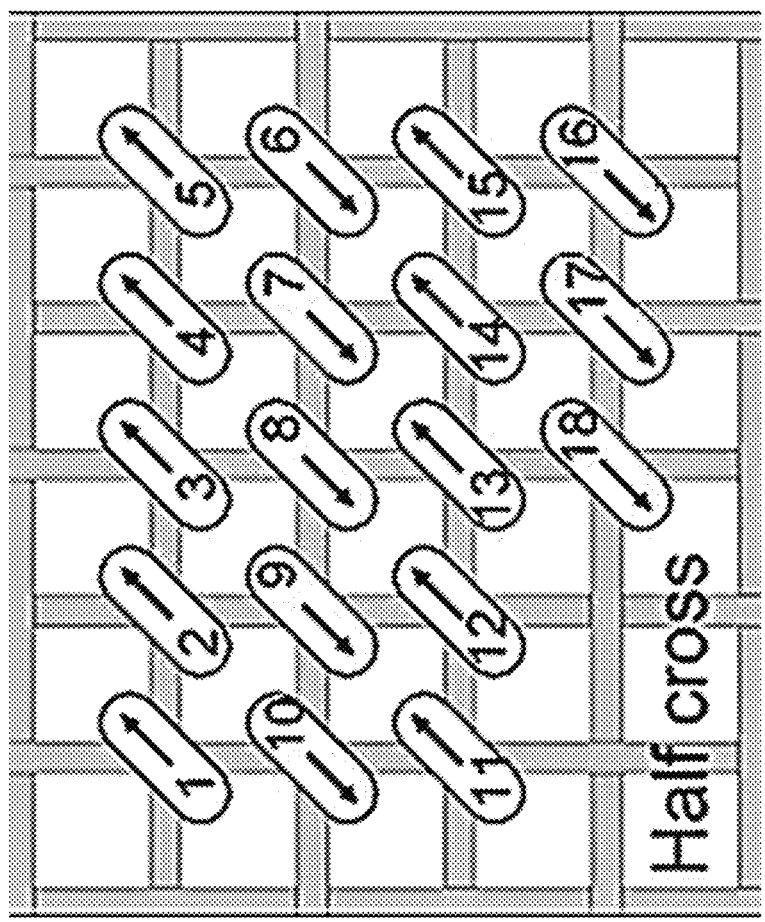
FIG. 6 is an illustration of a desired tent stitch pattern according to various embodiments of the present invention.

As noted above, the nursing pad 100 is formed of several layers. For further understanding, FIG. 5 provides an exploded-view illustration of the nursing pad 100. The proximal side 102 is formed by the surface layer 500. The surface layer 500 is, desirably, certified organic cotton that is woven to form a stable surface and the proximal side 102. The certified organic cotton surface provides a natural surface for the user's nipples to contact. In this desired aspect, a tent stitch is used with the organic cotton to create a special pattern and webbing or weaving of the organic cotton to form the surface layer 500. For example and as shown in FIG. 6, the desired tent stitch pattern is referred to as a "half-cross pattern." The "half-cross pattern" has a density that provides the perfect absorption/conduction of rapid absorption/pass through rate to the absorbent core layer. Other patterns or weaving formations can result in puddling and leakage, whereas the half-cross pattern provides a desired pattern and density of the certified organic cotton. In a desired aspect, the organic cotton surface is between approximately 10% to 20% (and desirably 15.5%) of the total mass of the nursing pad 100.

The next layer is a first tissue paper layer 502. The first tissue paper layer 502 is a thin layer formed of any suitable material that assists in preventing leakage of the absorbent core layer (described below) materials. As a non-limiting example, the first tissue paper layer 502 is formed of tissue paper.

Following the first tissue paper layer 502 is the absorbent core layer 504. The absorbent core layer 504 is a super absorbent core that absorbs excess milk like a sponge. The absorbent core layer 504 includes a combination of a super absorbent polymer (SAP) and fluff pulp that are mixed together/intergrade with one another. The super absorbent polymer (SAP) is any suitable SAP, a non-limiting example of which includes the SAP as sold by Sumitomo Seika Chemicals Co., Ltd. Further, the SAP can be provided in any desired amount to provide sufficient absorbency. As a non-limiting example, the SAP in the absorbent core layer 504 is between approximately 15% to 25% (and desirably 20%) of the total mass of the nursing pad 100.

The fluff pulp also assists in absorption of excess milk while providing a soft and comfortable product. As understood by those skilled in the art, fluff pulp is any suitable fluffy pulp-like material that provides for absorbency, bulk, and softness, a non-limiting example of which includes a pulp made from long fiber softwoods. Further, the fluff pulp can be provided in any desired amount to provide sufficient bulk, softness, and absorbency. As a non-limiting example, the fluff pulp in the absorbent core layer 504 is between approximately 35% to 50% (and desirably 44%) of the total mass of the nursing pad 100.

Following the absorbent core layer 504 is a second tissue paper layer 506. As was the case above with the first tissue paper layer 502, the second tissue paper layer 506 is a thin layer formed of any suitable material that assists in preventing leakage of the absorbent core layer (described below) materials. As a non-limiting example, the second tissue paper layer 506 is formed of tissue paper.

To seal the layers within the nursing pad 100 and prevent external leakage, the distal surface 104 is formed of a leakproof film layer 508. The leakproof film layer 508 is formed of a breathable waterproof film that prevents milk from leaking out of the nursing pad 100 and onto the user's clothing. As understood by those skilled in the art, the leakproof film layer 508 is formed of any breathable, yet leakproof material, a non-limiting example of which includes the breathable films as produced by Arkema, located at 420 rue d'Estienne d'Orves Colombes, Codes, France.

It is noted that the cotton surface layer 500 and leakproof film layer 508 are slightly larger in diameter than the internal tissue layers 502, 506, and absorbent core layer 504. Although not required, the cotton surface layer 500 and leakproof film layer 508 are slightly larger so that they can be directly adhered to one another (using glue or any other suitable adhesion technique) around their periphery and securely affix the other layers within the nursing pad 100. The internal layers 502, 504, and 506 can be placed loosely within the nursing pad 100 or, desirably, are adhered to one another using glue or any other suitable adhesion technique.

As can be appreciated by those skilled in the art, the nursing pad 100 described herein provides a safe and organic cotton surface that engages with the user's nipples while including a SAP that absorbs a significant amount of excess milk. It should also be noted that although specific percentages and components are described and illustrated as a desired and optimal implementation, it should be understood that the invention is not intended to be limited thereto as the percentage ranges can be modified and material substituted, removed, etc., provided that the resulting product includes the cotton layer that provides the "natural safety layer".

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A cotton surface nursing pad, comprising:
   a proximal side formed of a surface layer, the surface layer being formed of organic cotton;
   a distal side formed of a leakproof film layer; and
   an absorbent core layer affixed between the surface layer and leakproof film layer,
   wherein the surface layer is provided with a half-cross tent stitch pattern configured to enable rapid pass through of excess milk to the absorbent core layer.

2. The cotton surface nursing pad as set forth in claim 1, further comprising a first tissue layer adhered between the surface layer and absorbent core layer.

3. The cotton surface nursing pad as set forth in claim 2, further comprising a second tissue layer adhered between the absorbent core layer and leakproof film layer.

4. The cotton surface nursing pad as set forth in claim 3, wherein the absorbent core layer is formed of a combination of super absorbent polymer and fluff pulp.

5. The cotton surface nursing pad as set forth in claim 4, wherein the cotton surface nursing pad has a mass, with the organic cotton forming the surface layer being between 10% and 20% of the mass of the cotton surface nursing pad.

6. The cotton surface nursing pad as set forth in claim 5, wherein the super absorbent polymer in the absorbent core layer is between 15% to 25% of the mass of the cotton surface nursing pad.

7. The cotton surface nursing pad as set forth in claim 6, wherein the fluff pulp in the absorbent core layer is between 35% to 50% of the mass of the cotton surface nursing pad.

8. The cotton surface nursing pad as set forth in claim 7, wherein the organic cotton forming the surface layer is approximately 15.5% of the mass of the cotton surface nursing pad.

9. The cotton surface nursing pad as set forth in claim 8, wherein the super absorbent polymer in the absorbent core layer is approximately 20% of the mass of the cotton surface nursing pad.

10. The cotton surface nursing pad as set forth in claim 9, wherein the fluff pulp in the absorbent core layer is approximately 44% of the mass of the cotton surface nursing pad.

11. The cotton surface nursing pad as set forth in claim 1, wherein the absorbent core layer is formed of a combination of super absorbent polymer and fluff pulp.

12. The cotton surface nursing pad as set forth in claim 11, wherein the cotton surface nursing pad has a mass, and wherein the super absorbent polymer in the absorbent core layer is between 15% to 25% of the mass of the cotton surface nursing pad.

13. The cotton surface nursing pad as set forth in claim 11, wherein the cotton surface nursing pad has a mass, and wherein the fluff pulp in the absorbent core layer is between 35% to 50% of the mass of the cotton surface nursing pad.

14. The cotton surface nursing pad as set forth in claim 11, wherein the cotton surface nursing pad has a mass, and wherein the super absorbent polymer in the absorbent core layer is approximately 20% of the mass of the cotton surface nursing pad.

15. The cotton surface nursing pad as set forth in claim 11, wherein the cotton surface nursing pad has a mass, and wherein the fluff pulp in the absorbent core layer is approximately 44% of the mass of the cotton surface nursing pad.

16. The cotton surface nursing pad as set forth in claim 1, wherein the cotton surface nursing pad has a mass, with the organic cotton forming the surface layer being between 10% and 20% of the mass of the cotton surface nursing pad.

17. The cotton surface nursing pad as set forth in claim 1, wherein the cotton surface nursing pad has a mass, and wherein the organic cotton forming the surface layer is approximately 15.5% of the mass of the cotton surface nursing pad.

* * * * *